US009554355B2

(12) United States Patent
Higgins et al.

(10) Patent No.: US 9,554,355 B2
(45) Date of Patent: Jan. 24, 2017

(54) METHODS AND SYSTEMS FOR PROVIDING NOTIFICATIONS BASED ON USER ACTIVITY DATA

(71) Applicant: eBay Inc., San Jose, CA (US)

(72) Inventors: Krystal Rose Higgins, Campbell, CA (US); John Tapley, San Jose, CA (US)

(73) Assignee: eBay Inc., San Jose, CA (US)

( * ) Notice: Subject to any disclaimer, the term of this patent is extended or adjusted under 35 U.S.C. 154(b) by 144 days.

(21) Appl. No.: 14/446,247

(22) Filed: Jul. 29, 2014

(65) Prior Publication Data

US 2016/0037482 A1 Feb. 4, 2016

(51) Int. Cl.
  *H04M 3/42* (2006.01)
  *H04W 68/00* (2009.01)
  *H04W 4/16* (2009.01)
  *H04W 4/02* (2009.01)
  *H04W 4/04* (2009.01)
  (Continued)

(52) U.S. Cl.
  CPC .......... *H04W 68/005* (2013.01); *A61B 5/1118* (2013.01); *G06Q 10/10* (2013.01); *H04W 4/027* (2013.01); *H04W 4/046* (2013.01); *H04W 4/16* (2013.01)

(58) Field of Classification Search
  CPC ...... H04L 12/588; H04L 41/147; H04L 67/02; H04L 67/16; H04L 67/306; H04L 51/32; H04L 51/38; H04L 63/104; H04L 65/403; H04L 67/10; H04L 45/02; H04W 4/046; H04W 4/206; H04W 12/06; H04W 4/16; H04W 8/18; H04W 4/008
  USPC .... 455/414.1, 418, 41.2, 404.2, 26.1, 426.1, 455/456.1
  See application file for complete search history.

(56) References Cited

U.S. PATENT DOCUMENTS

| 7,890,085 B2 | 2/2011 | Chiu et al. |
| 8,483,665 B2 | 7/2013 | Kissinger et al. |
| 8,558,693 B2 | 10/2013 | Martin et al. |
| (Continued) | | |

FOREIGN PATENT DOCUMENTS

| EP | 1505529 A1 | 2/2005 |
| WO | WO-2010107735 A1 | 9/2010 |
| WO | WO-2016018788 A1 | 2/2016 |

OTHER PUBLICATIONS

"International Application Serial No. PCT/US2015/042192, International Search Report mailed Oct. 13, 2015", 3 pgs.
(Continued)

*Primary Examiner* — Fred Casca
(74) *Attorney, Agent, or Firm* — Schwegman Lundberg & Woessner, P.A.

(57) ABSTRACT

Systems and methods are presented for providing notifications based on user activity data. In some embodiments, a method is presented. The method may include accessing first sensor data associated with a first activity of a user. The method may also include determining that the user is engaged in the first activity based at least in part on the first sensor data, receiving a notification while the user is engaged in the first activity, and determining to not present or in other words, hold the notification while the user is engaged in the first activity. In some embodiments, the method may also include accessing second sensor data associated with the user, determining that the user is no longer engaged in the first activity based at least in part on the second sensor data, and presenting the notification while the user is no longer engaged in the first activity.

18 Claims, 8 Drawing Sheets

(51) Int. Cl.
  *A61B 5/11* (2006.01)
  *G06Q 10/10* (2012.01)

(56) References Cited

U.S. PATENT DOCUMENTS

| | | | |
|---|---|---|---|
| 2002/0163572 A1* | 11/2002 | Center, Jr. | H04N 21/44218 348/14.08 |
| 2008/0240384 A1 | 10/2008 | Suryanarayana et al. | |
| 2009/0249247 A1 | 10/2009 | Tseng et al. | |
| 2013/0090103 A1* | 4/2013 | Kim | H04M 1/72577 455/418 |
| 2014/0058780 A1 | 2/2014 | Gilzean et al. | |
| 2015/0161876 A1* | 6/2015 | Castillo | G08B 21/0446 340/539.11 |

OTHER PUBLICATIONS

"International Application Serial No. PCT/US2015/042192, Written Opinion mailed Oct. 13, 2015", 5 pgs.

\* cited by examiner

METHODS AND SYSTEMS FOR PROVIDING NOTIFICATIONS BASED ON USER ACTIVITY DATA

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2014, eBay Inc. All Rights Reserved.

TECHNICAL FIELD

The subject matter disclosed herein generally relates to mobile and wearable device technology, in some example embodiments, the present disclosures relate to systems and methods for providing notifications based on user activity data.

BRIEF DESCRIPTION OF THE DRAWINGS

Some embodiments are illustrated by way of example and not limitation in the figures of the accompanying drawings.

DETAILED DESCRIPTION

As technology becomes ever more integrated into daily human interactions, users have at times expressed a backlash against some aspects of technological functionality that have become distracting, inconveniencing or even potentially harmful. For example, movie goers often loathe any instances of a cell phone ring going off in a theater. As another example, a jogger may not want to be inconvenienced by any alerts or notifications during a focused run. As another example, texts received while driving can be the cause of a grisly accident. It is therefore desirable to improve methods for receiving notifications in mobile and other wearable devices.

Aspects of the present disclosure are presented for receiving a notification, determining when it may be appropriate to present the notification to a user based on the user's activity, and displaying or other otherwise presenting the notification on a mobile device for the user during an appropriate time. In some example embodiments, data from one or more wearable devices may be used to determine or estimate a current activity of the user. For example, data from a Global Positioning System (GPS) combined with accelerometer data may be used to determine or estimate that the user is driving in a car and should not be disturbed while driving. As another example, heart rate and other data about the user's health may be obtained to estimate or determine the user is participating in vigorous exercise and may not want to be disturbed during that time. During these periods, a mobile device may receive a notification, but may deliberately not display the notification during these example activities and may wait until a more appropriate time to display the notification. These and other example embodiments will be described in more detail below.

Figure 1:
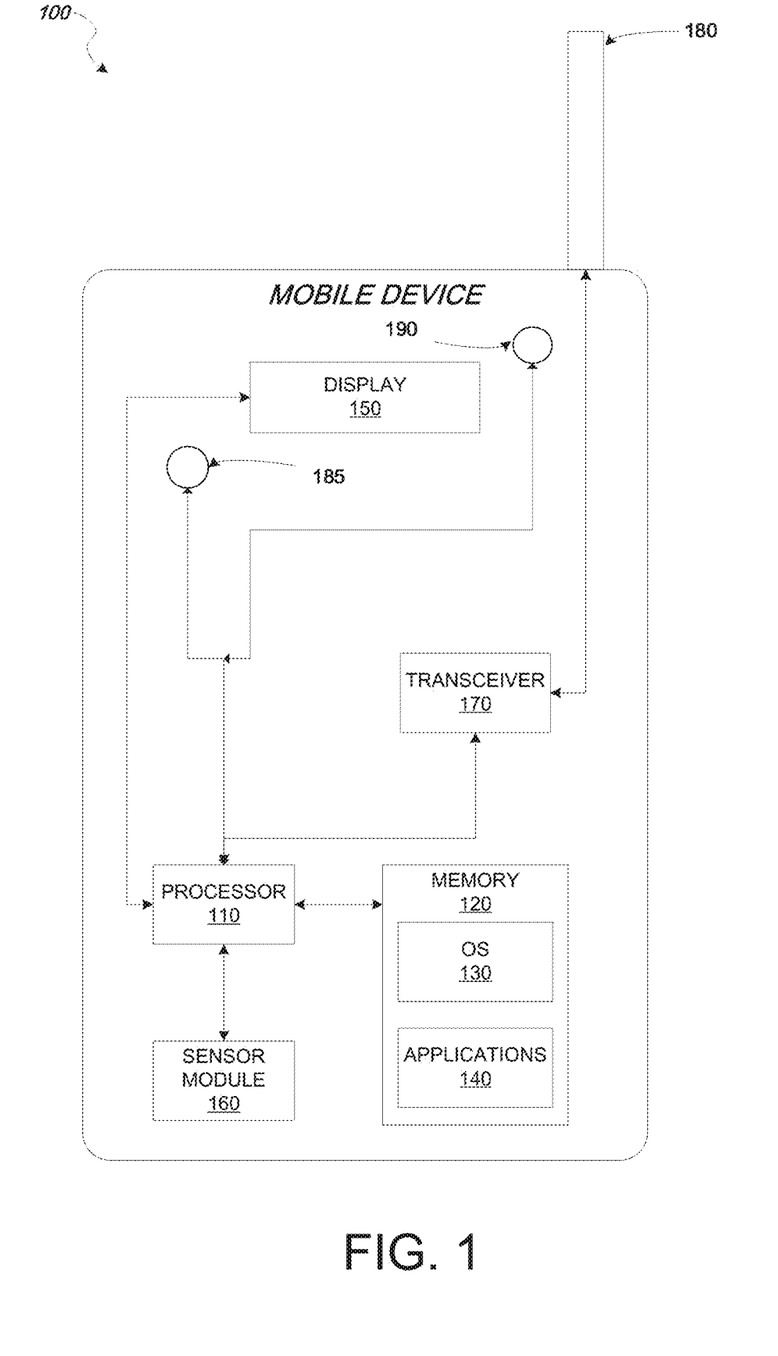
FIG. 1 is block diagram illustrating a mobile device suitable for providing notifications based on user activity data, according to some example embodiments.

Referring to FIG. 1, a block diagram illustrating a mobile device 100 is presented, according to some example embodiments. The mobile device 100 may be configured to receive a notification (e.g., a text message, a message from an application, a calendar reminder), access various sensor data associated with the mobile device, determine, or at least estimate, a user activity based on the sensor data, and determine an appropriate time to present the notification based on the determined or estimated user activity, according to at least some example embodiments. Microphone 185 and image recorder 190 may be configured to record various audio recordings and video recordings, respectively. In some cases, the microphone 185 and image recorder 190 may be included into a single component of the mobile device 100, such as an audio/visual (AV) recorder known to those with skill in the art.

A sensor module 160 may be configured to access various types of sensor data besides audio and visual sensor data, such as accelerometer and gyroscope data, where one or more accelerometers or gyroscopes (not shown) are built in to the mobile device 100. Other example types of sensor data that can be accessed by the sensor module 160 will be described in more detail in FIG. 3, below. The data from microphone 185, image recorder 190, and sensor module 160 may be processed by processor 110. The processor 110 may be any of a variety of different types of commercially available processors suitable for the mobile devices 100 (e.g., an XScale architecture microprocessor, a Microprocessor without Interlocked Pipeline Stages (MIPS) architecture processor, or another type of processor). The processor 110 may be configured to operate applications 140, which may be configured to determine a user activity based on sensor data from one or more of the microphone 185, image recorder 190, and sensor module 160, and may determine an appropriate time to present a notification to the user based on the determined user activity.

A memory 120, such as a random access memory (RAM), a Flash memory, or other type of memory, is typically accessible to the processor 110. The memory 120 may be adapted to store an operating system (OS) 130, as well as the application 140, such as a mobile application for recording a conversation or event based on the identified natural gesture or natural phrase.

The processor 110 may be coupled, either directly or via appropriate intermediary hardware, to a display 150 and to one or more input/output (I/O) devices (not shown), such as a keypad, a touch panel sensor, a microphone, a controller, a camera, and the like. Similarly, in some embodiments, the processor 110 may be coupled to a transceiver 170 that interfaces with an antenna 180. The transceiver 170 may be configured to both transmit and receive cellular network signals, wireless data signals, or other types of signals via the antenna 180, including information related to a notification, depending on the nature of the mobile device 100. In some example embodiments, the processor 110 may include a plurality of processors or modules configured to perform various operations according to aspects of the present disclosure.

Figure 2:
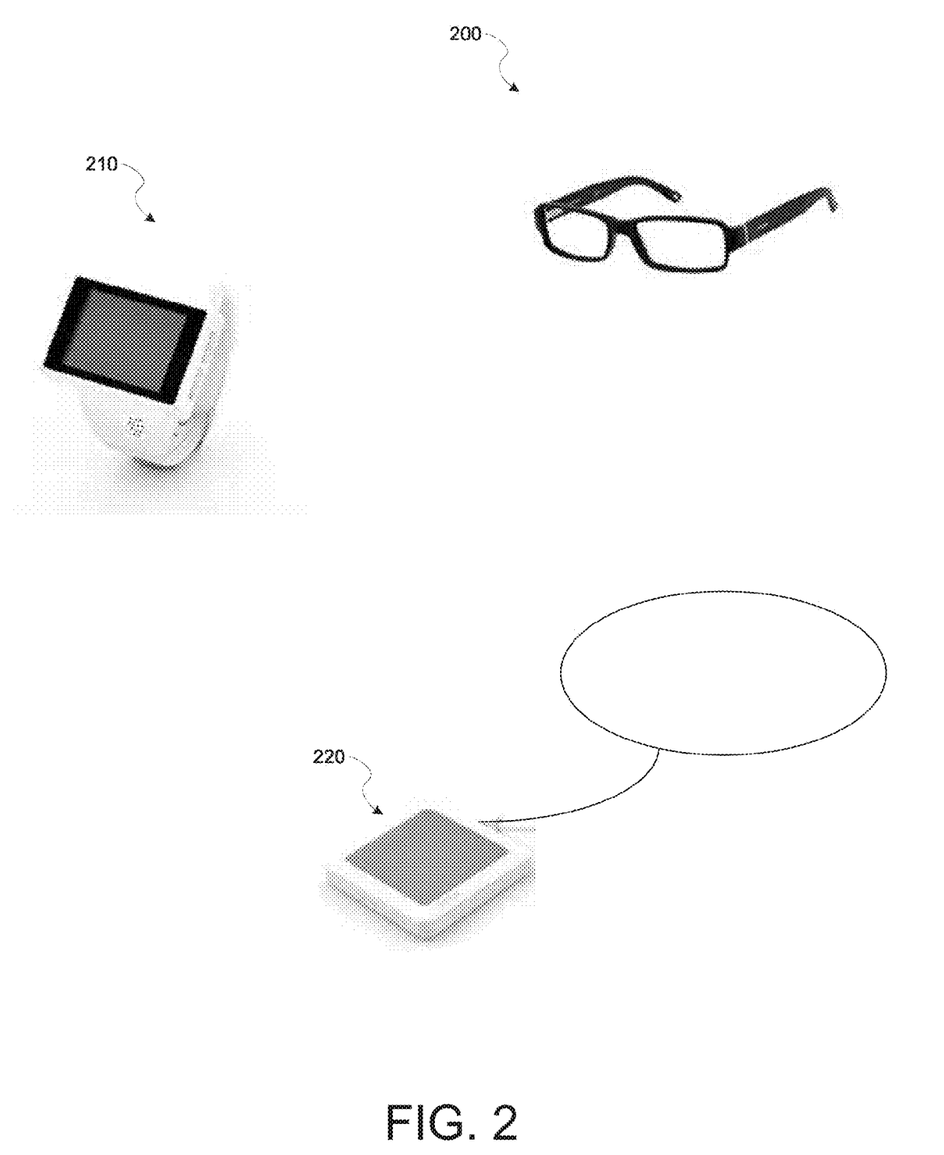
FIG. 2 is a set of images of various wearable devices suitable for providing notifications based on user activity data, according to some example embodiments.

Referring to FIG. 2, other examples of mobile devices that can be used in aspects of the present disclosure are presented. The devices presented in FIG. 2 may be wearable devices that are configured to access various sensor data in order to determine, or at least estimate, a user's activity, according to some example embodiments. In some cases, the wearable devices may also be configured to receive a notification and may determine an appropriate time to present the notification based on the user's activity. For example, glasses 200 may be specially equipped with micro viewing technology, one or more microphones, one or more micro cameras, and one or more microprocessors that collectively may be capable of determining a user's activity. Example methods for accomplishing this will be described in more detail below. The glasses 200 may be similar to wearable digital devices such as Google Glass®, and other glasses with digital technology. As another example, a smart watch 210 may be specially equipped with heart-rate monitoring sensors, a pedometer, an altimeter, or other sensors useful determining if a user is engaged in some kind of exercise. As another example, wearable device 220 may be a digital device wearable around a user's neck. The wearable device 220 may possess similar functionality as those described in the glasses 200 or the smart watch 210. In some example embodiments, wearable devices can also be configured to access some or all of the various types of sensor data described in FIG. 3, below. Other example wearable devices can include a Fitbit® and a mobile device attached to a shoulder strap.

In some example embodiments, a combination of devices can be configured to facilitate aspects of the present disclosure. For example, a first wearable device can be configured to receive notifications via wireless transmission means. A second wearable device can be configured to determine, or at least estimate, an activity of the user through various sensor data. The two devices can be communicatively coupled via Bluetooth® or other means apparent to those with skill in the art. In general, other wearable devices apparent to those with skill in the art and consistent with the disclosures herein may also be capable of performing the functions according to aspects of the present disclosure and embodiments are not so limited.

Figure 3:
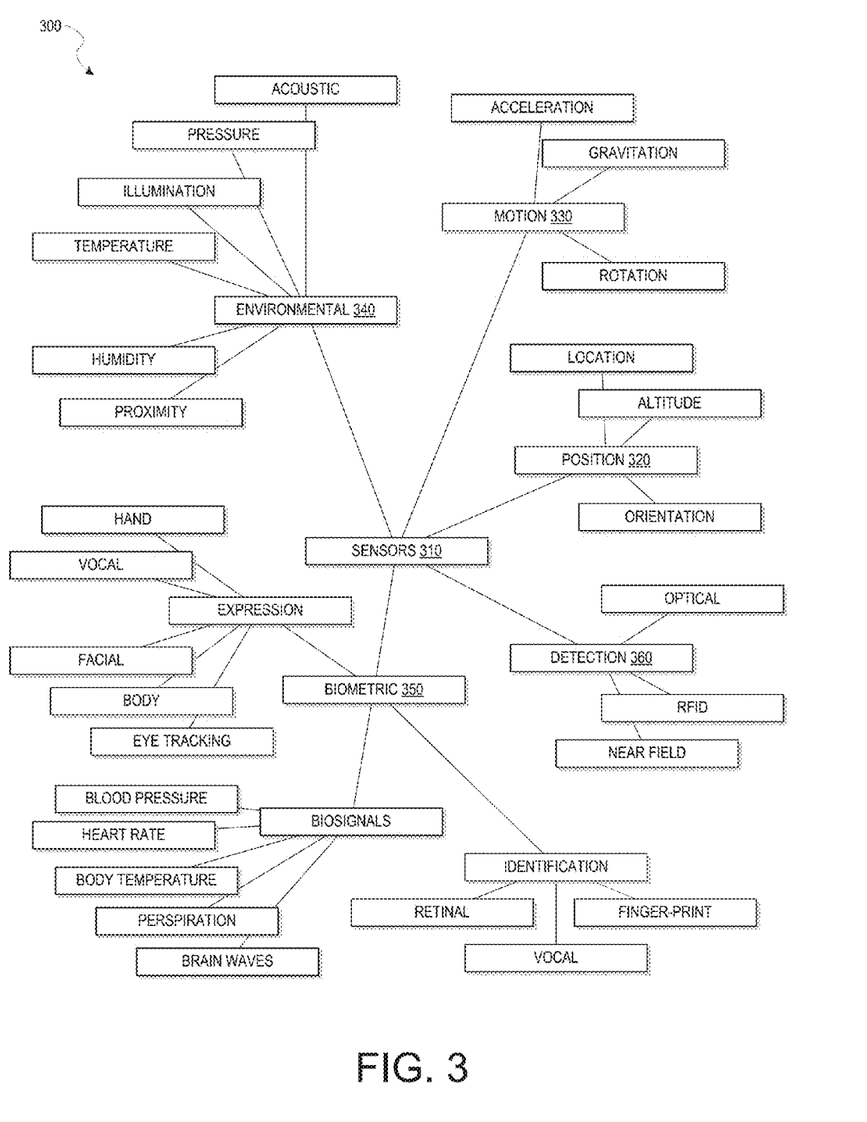
FIG. 3 is an illustration showing example types of sensor data and types of sensors, suitable for providing notifications based on user activity data, according to some example embodiments.

Referring to FIG. 3, example chart 300 depicts example sensors, gauges, and measurement components 310 that may be included in any one of the devices depicted in FIGS. 1 and 2, according to some example embodiments. Any suitable combination of sensors, gauges, and measurement components (collectively referred to as "sensor components" 310) may be implemented to facilitate the functionality described herein. FIG. 3 merely depicts non-limiting examples of the sensor components 310 and many other components that provide various sensor data and may be included in any one of the example devices 100, 200, 210, or 220. The sensor components 310 may receive, detect, measure, or capture sensor data associated with physical properties or attributes. The sensor components 310 may provide, produce, transmit, or communicate the sensor data or other indications associated with physical properties or attributes. Thus, the sensor data corresponding to the sensor components 310 may be accessible to all, or some, of the modules described in FIG. 1, as well as the devices 200, 210, 220 described in FIG. 2. For example, the sensor module 160 may include one or more sensor components 310.

In various example embodiments, the sensor components 310 may include position components 320. The position components 320 may include location sensors (e.g., GPS receiver component), altitude sensors (e.g., altimeters or barometers that detect air pressure from which altitude may be derived), orientation sensors (e.g., magnetometers that provide magnetic field strength along the x, y, and z axes), and the like. In some example embodiments, the position components 320 may provide position data such as latitude, longitude, altitude, and a time stamp. The position data may be provided at a regular update rate (e.g., 10 updates per second) that may be configurable.

In further example embodiments, the sensor components 310 may include motion components 330. The motion components 330 may include acceleration sensors (e.g., an accelerometer), gravitation sensors, rotation sensors (e.g., a gyroscope), and so forth. The motion components 330 may provide motion data such as velocity, acceleration, rotational vectors, or other force measurements along two or three dimensions. Similar to the position components 320, the motion components 330 may provide the motion data at a regular update rate that may be configurable.

In some further example embodiments, the sensor components 310 may include environmental components 340. The environmental components 340 may include illumination sensors (e.g., a photometer), temperature sensors (e.g., one or more thermometers that measure ambient temperature), humidity sensors, pressure sensors (e.g., a barometer), acoustic sensors (e.g., one or more microphones that detect background noise), proximity sensors (e.g., an infrared sensor that detects nearby objects), and so on. The environmental components 340 may measure various physical parameters to provide an indication or signal corresponding to the physical environment surrounding the environmental components 340.

In some example embodiments, the sensor components 310 may include biometric components 350 that may detect expressions, measure biosignals, or identify people, among other functions related to biology. For example, the biometric components 350 may include expression components to detect expressions (also referred to as kinesics) such as hand gestures (e.g., an optical component to detect a hand gesture or a Doppler component to detect hand motions), vocal expressions (e.g., a microphone to detect changes in voice pitch that may indicate tension), facial expressions (e.g., a camera to detect expressions or micro-expressions of a person such as a smile), body gestures, and eye tracking (e.g., detecting the focal point of a person's eyes or patterns in eye movement). The biometric components 350 may also include, for example, biosignal components to measure biosignals such as blood pressure, heart rate, body temperature, perspiration, brain waves (e.g., as determined by a electroencephalogram), and the like. In further examples, the biometric components 350 may include identification components to identify people, such as retinal scanners (e.g., a camera component), vocal detectors (e.g., a microphone to receive audio data for voice identification), facial detectors, finger-print detectors, and electroencephalogram sensors (e.g., to identify a person via unique brain wave patterns).

In still further example embodiments, the sensor components 310 may include detection components 360 that may detect a variety of identifiers. For example, the detection components 360 may include Radio Frequency Identification (RFID) tag reader components, Near Field Communication (NFC) smart tag detection components, optical reader components (e.g., an optical sensor to detect one-dimensional bar codes such as a Universal Product Code (UPC) bar code, multi-dimensional bar codes such as a Quick Response (QR) code, Aztec code, Data Matrix, Dataglyph, MaxiCode, PDF417, Ultra Code, Uniform Commercial Code Reduced Space Symbology (UCC RSS)-2D bar code, and other optical codes), and acoustic detection components (e.g., microphones to identify tagged audio signals). In additional, a variety of information may be derived via various communication components such as location via Internet Protocol (IP) geo-location, location via signal triangulation, location via detecting a NEC beacon signal that may indicate a particular location, and so forth.

In general, it may be apparent to persons with skill in the art of other types of sensor components and example implementations that can be included in one or more of the devices 100, 200, 210, or 220, consistent with the disclosures herein, and embodiments are not so limited.

Figure 4:
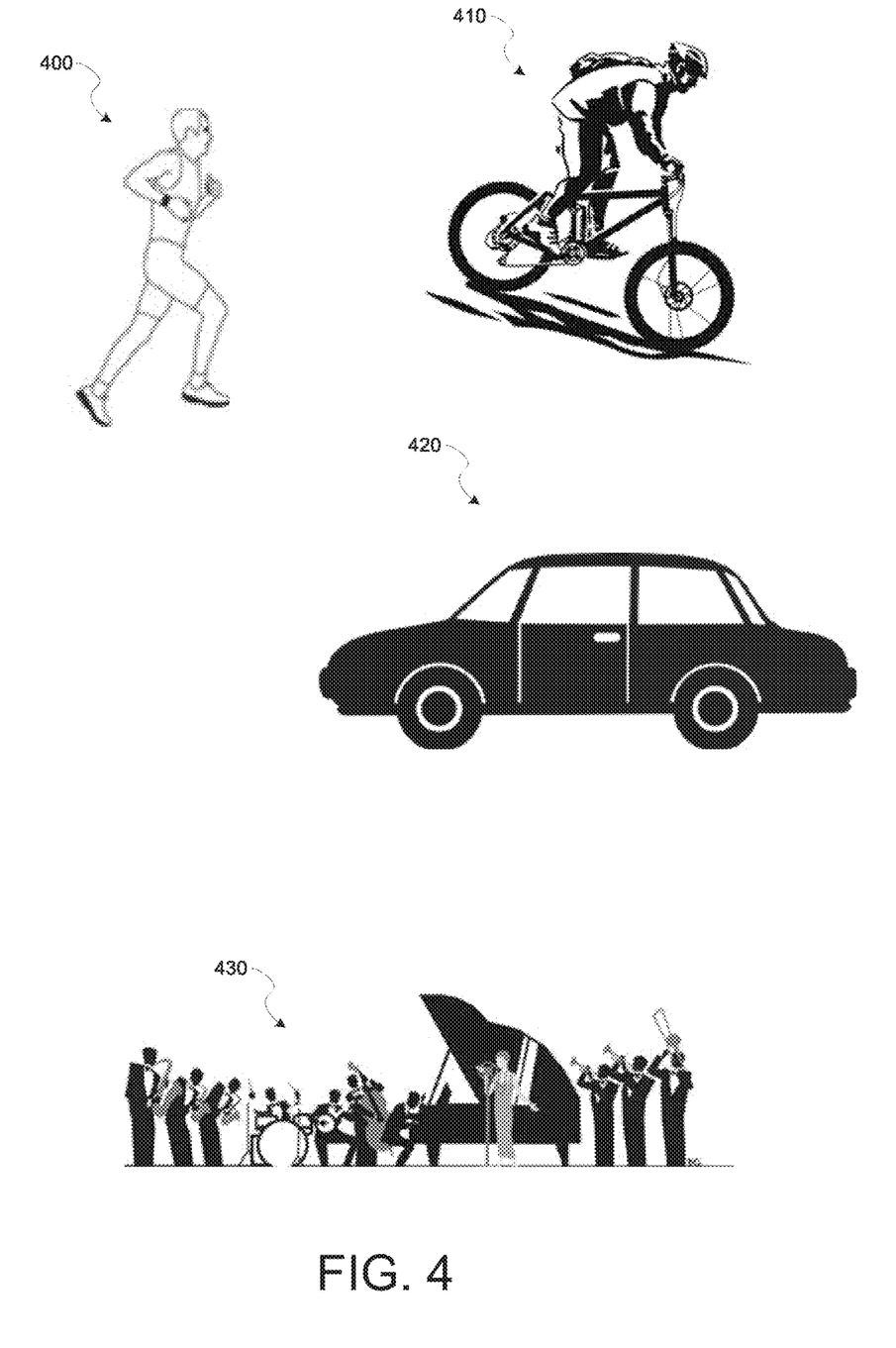
FIG. 4 illustrate example activities of a user, during which notifications may be withheld, according to some example embodiments.

Referring to FIG. 4, illustrations showing example activities that may be determined by aspects of the present disclosure are presented. For example, illustration 400 shows a user who may be going out for a run or jog. The user may be wearing a wearable device, such as the wearable device 210, or carrying a mobile device, such as the mobile device 100. While the user is running, the wearable device 210 may be configured to access various sensor data related to the user's biometric characteristics. For example, the wearable device 210 may include sensors that can measure the user's heart rate, blood pressure, body temperature, or level of perspiration, consistent with the descriptions in FIG. 3, according to some embodiments. Thus, while the user is running, the wearable device 210 may be able to detect that the user's heart rate has increased dramatically. Also, the wearable device 210 may be able to detect that the user's body temperature has risen, his level of perspiration has increased, along with his blood pressure. Based on these detected biometric attributes, the wearable device 210 may be able to estimate or determine that the user is engaged in exercise if one or more of these biometric attributes satisfies some threshold criterion, based on the measured sensor data. For example, aspects of the present disclosure may determine that the user is jogging if a detected heart rate rises above 140 beats per minute (bpm). In some cases, the jogging activity can be corroborated based on detecting that the user's body temperature rises above a certain threshold, such as above 100° F. As another example, the jogging activity can be corroborated based on detecting that the user's blood pressure satisfies a certain criterion, such as detecting systolic blood pressure between 160 and 220 while diastolic blood pressure changes minimally. Other sensor data can be used in combination to make a determination that the user is jogging. For example, the wearable device 210 may also include a pedometer, which can be configured to count a number of steps while the user is jogging, as well as possibly compute a rate of steps in order to determine that the user's steps have increased in pace, consistent with jogging. As another example, an altimeter or an accelerometer can also be included in the wearable device 210, and may be configured to measure motion of the user, consistent with jogging, such as a bouncing motion while running. Other examples sensors can be incorporated to determine that the user is running, as is apparent to those with skill in the art, and embodiments are not so limited.

In some example embodiments, it may be specified, by either the user or by pre-programming, for example, that the user should not be disturbed with any electronic notifications when the user is engaged in exercise such as running or jogging. For example, it may be desirable for the user to have a concerted, focused exercise period, and thus distractions should be minimized wherever possible. Therefore, after having detected that the user is engaged in exercise, aspects of the present disclosure may deliberately withhold presenting any electronic notifications for as long as it is determined that the user is still engaged in exercise. For example, the user may receive a text message, or the user may have his mobile device configured to notify him whenever he receives new email. However, if these notifications occur while it is detected that he is exercising, these notifications may be stored, but not displayed at first. In some example embodiments, the same or different sensors used to detect that the user is exercising could also be used to detect when the user has stopped exercising, or is in his cool-down routine. For example, the wearable device 210 can detect that the user's heart rate has decreased to a level resembling a resting heart rate, or that the user has stopped moving or at least has slowed his stepping pace based on pedometer or accelerometer data. The wearable device 210 may then display the notification on its display screen, or otherwise send some other signal letting the user know that he has one or more notifications. As an example, the processor 110, which may be included in the wearable device 210, may be configured to access sensor data from the sensor module 160, which may include any or all of the sensors 310. The processor 110 may determine based on the sensor data that the user is engaged in exercise or otherwise not in a position to be disturbed, and may then determine to deliberately withhold present any electronic notifications for as long as it is determined that the user is still engaged in exercise.

As another example, illustration 410 is presented for a user that may be engaged in a mountain bike ride. The user may have in his possession one or more of his mobile device 100, the wearable device 210, or the glasses 200 to visually record his bike ride, as examples. It may be desirable for the user to focus his attention on his bike ride, for safety or for pleasure purposes, as examples. Thus, the user may not want to be disturbed by any electronic notifications during his bike ride.

In some example embodiments, a mobile or wearable device of the user may be configured to detect that the user is engaged in the bike ride, and thus may withhold presenting any electronic notifications for as long as it is determined that the user is still bike riding. For example, accelerometer data from one or more accelerometers included in the user's mobile device 100 may detect that the user is accelerating at a rate quicker than merely jogging, but slower than driving a car, which may be consistent with a bike ride pattern. In addition, the user's mobile device 100 may also detect biometric readings consistent with light or moderate exercise while the user is biking, which could disambiguate the user riding a bike over other kinds of mobile activity, such as riding a scooter or driving in a slow-moving vehicle.

In some example embodiments, consistent with the previous jogging example, the mobile device 100 may determine when the user has finished his bike ride or at least stopped moving on his bike, based on the same types of sensors used to determine that the user was riding his bike. For example, the mobile device 100 may detect a corresponding deceleration consistent with the user stopping. In addition, the user's heart rate, blood pressure, and other biometric signals may be detected to be consistent with the user stopping his bike ride or going into a cool-down routine. At this point, aspects of the present disclosure may present any notifications received during the user's bike ride, based on either a user specification or preprogramming that indicated that an appropriate time to present notifications is when the user is resting or stopping. As an example, the processor 110 in the mobile device 100 may instruct the display 150 to display any notifications received during the user's bike ride.

In another example, illustration 420 is presented for a user that is driving a car. The user may be carrying the mobile device 100 or wearable device such as any of the wearable devices 200, 210, or 220. Sensor data of the mobile device 100 or wearable devices 200, 210, or 220, can be used to determine or estimate that the user is starting to drive the car. For example, one or more accelerometers can measure the acceleration experienced while in the vehicle to determine that the car is moving. Based on the measurement of acceleration over a period of time, the velocity of the vehicle can be determined. It can also be determined when the vehicle has slowed down sufficiently or stopped, based on a corresponding deceleration over a period of time. Thus, until it is determined that enough deceleration has occurred, the user's mobile device 100 or wearable device may deliberately withhold presenting any electronic notifications on its screen or through other means to the user. In other cases, the notification may simply be redirected to another display screen or presented in a less distracting manner. For example if the user can connect his mobile device 100 to a digital screen on the dashboard of his car, in some example embodiments, the notification may simply be presented on the dashboard instead of being presented in his mobile device 100 that may force him, or compel him, to look away from the road. Obviously, it can be desirable to minimize distractions of the driver, including receiving any messages or notifications that the user does not have any control of. Aspects of the present disclosure can be helpful in minimizing distractions by disallowing any electronic notifications from having even the chance to distract the driver, based on example techniques described herein. In the cases where the user is not driving, rather is merely riding in the car, in some example embodiments, a setting in an application can be applied to allow notifications in spite of detecting that the user is moving in a vehicle.

In yet another example, illustration 430 is presented for a user that is attending a social event, such as a concert or party with a live band. In this context, the user may wish to not be disturbed by any notifications, as she may wish to maintain her focus on the event. Alternatively, the user may wish to see messages or notifications only in private, so as to not appear distracted, or because she is expecting certain messages of a sensitive nature and does not want to be notified of the messages in public, as examples.

Various sensors from her mobile device 100 or wearable device 200, 210, or 220 may be configured to pick up ambient noise, including a volume (e.g. decibels) level. One or more processors of the mobile device 100 or wearable device 200, 210, or 220 may be configured to process the noise, determine if music is being played, for example, or determine if the noise level around the user exceeds some threshold noise level.

In some example embodiments, location data can be obtained simultaneously. For example, it can be determined, based on obtained geolocation data or sensor data for accessing RFID information with known locations, that the user is located in a known concert hall, restaurant, convention hall, or in general any location that can be hosting a social gathering event. In this way, aspects of the present disclosure, for example the processor 110, can determine if the user is in a loud area or is in some social gathering. Based on this determination, any electronic notifications received while it is still determined that the user remains in that location or the social gathering is still continuing can be deliberately withheld until it is determined that the user has left that venue or that the user has moved to a quieter or more private location.

In general, aspects of the present disclosure allow for a multitude of user activities to be determined or at least estimated based on various sensor data received from one or more combinations of sensors that can be available on mobile devices or wearable devices. While a number of example scenarios have been presented, certainly many other activities could be detected in similar or analogous ways apparent to those with skill in the art and according to aspects of the present disclosure, and embodiments are not so limited.

Figure 5:
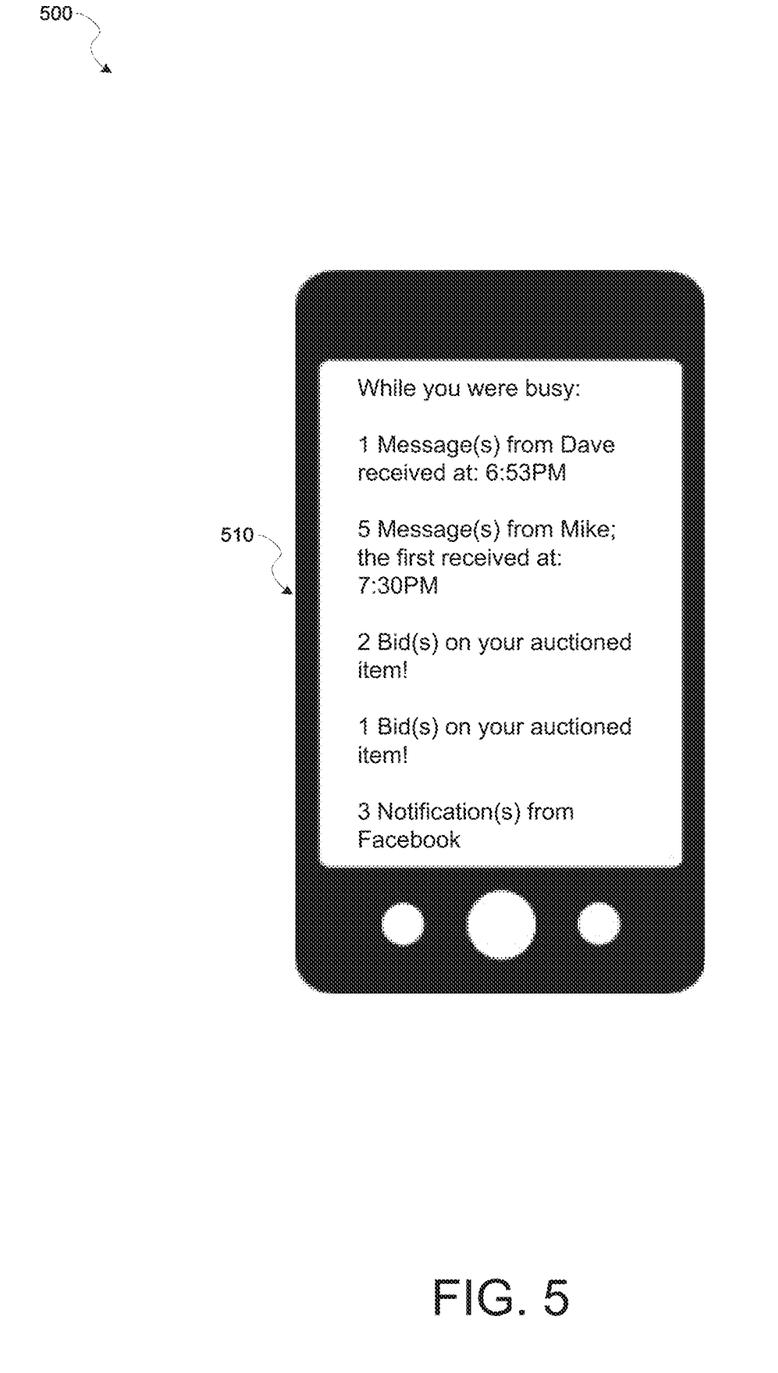
FIG. 5 is an example display for providing notifications based on user activity data, according to some example embodiments.

Referring to FIG. 5, illustration 500 shows an example display screen 510 for presenting example types of notifications that may have been received but were deliberately withheld while the user was engaged in some activity detected or estimated by various sensor data, according to some example embodiments. The display screen 510 may be displayed on the mobile device 100, or analogous versions may be displayed or presented in the wearable devices 200, 210, or 220. For example, the text shown in the display screen 510 can be projected onto one or more lenses of the wearable device 200. Alternatively, a formatted version of the text in the display screen 510 may be presented on a display screen in the wearable device 210 or 220.

The text in the display screen 510 indicates that the user was "busy," the determination of which can be ascertained based on the processing of various sensor data obtained from one or more sensors in the mobile device 100 or wearable device 200. The example activities can be any one of the example activities described in FIG. 4, or any other example activity consistent with the present disclosures herein and apparent to those with skill in the art. Similarly, based on the same or different sensors, various other sensor data could determine that the user is no longer "busy," at which point aspects of the present disclosure may display text, such as the text in display 510, to the user. For example, the processor 110 may determine based on the sensor day that the user is no longer busy, and may then display the notification through the display 150. Messages (e.g., texts) and quantity of the messages can be continuously received, compiled, or stored, but may be deliberately withheld from being presented until it is determined, based on various sensor data, that the user is presently engaged in an activity that is deemed appropriate to present the notifications.

In some example embodiments, various metadata could be presented in the display screen as well. For example, because the user may receive a glut of messages or notifications all at once, a timestamp of when the messages or notifications were initially received can be presented in the display screen 510. As another example, it may be helpful to display from which application or messaging system the notification arises from. Other variants are also possible, such as providing links to access the various notifications that can be clicked on or tapped.

Figure 6:
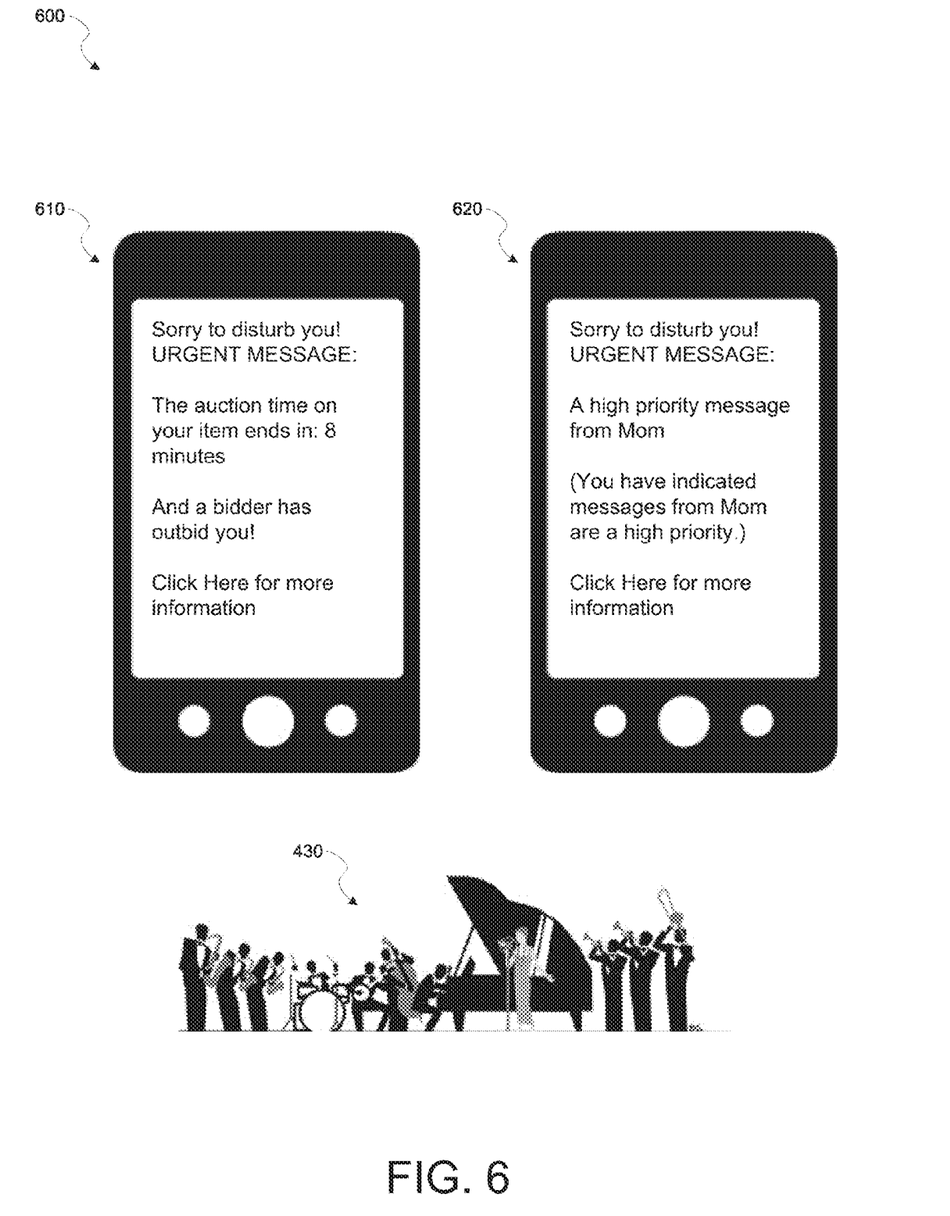
FIG. 6 is another example scenario and corresponding displays for providing notifications based on user activity data, according to some example embodiments.

Referring to FIG. 6, in some example embodiments, the deliberate withholding of certain messages or notifications can be overridden or modified slightly to account for urgent notifications or messages with a specified higher priority. The specified priority (either as to what has a higher priority or lower priority) can be indicated by a priority specification input. For example, the scenario presented in illustration 600 can represent the user being at a concert or some other music event, similar to the scenario presented in illustration 430. In that example scenario, the user may not normally receive any electronic notifications until it is determined, or at least estimated, that the user is in a quieter area or a more private location. However, there may still be some notifications that the user may want to know about immediately, that are considered higher priority than focusing on the event at hand, or may be considered important enough to be notified of in spite of being in a public place. The processor 110 may receive a priority specification input from the user of the mobile device 100 to override or modify account settings to display or receive urgent notifications based on the user specifications. In some example embodiments, some types of notifications may be predetermined as having a higher (or lower) priority compared to other notifications. These distinctions may be indicated by a priority specification.

For example, as shown in example display 610, the user may have bid on an item in an online auction. While the user is attending the concert illustrated in scenario 430, the time for the online auction may be set to expire. In some example embodiments, a setting can specify that auction notifications be deemed an urgent message or at least time sensitive, and therefore notifications about the auction may be presented to the user immediately upon receipt, even when it is determined that it is not otherwise appropriate to send the user notifications. In some cases, a setting can specify that only auction notifications be presented to the user if the auction time is about to expire within a certain predetermined amount of time (e.g., the next 30 minutes or an hour). In all other cases, the user will not be disturbed with any notifications from the auction while attending the event illustrated in 430.

As another example, the user can spec a higher priority to messages or notifications received from certain people, applications, or other specific sources. For example, as shown in display 620, the user may have specified that any text messages received from the phone number labeled "Mom" be given a high priority label. In some example embodiments, all sources designated with the "high priority" label is allowed to be presented to the user when the user would otherwise not be, due to the determined or estimated activity the user is engaged in. In some cases, a software application consistent with aspects of the present disclosure may have certain sources pre-designated as high priority sources. In other cases, the user may need to specify which sources can be presented as urgent messages. Obviously, in other cases, some combination of pre-designations and user specifications are available, and embodiments are not so limited. As an example, the software application may be stored in the memory 120 of mobile device 100, which can be accessed and executed by the processor 110.

Similarly, in some example embodiments, other types of filters or designations can be specified. For example, a "private" label may be specified for one or more sources, where the messages from the "private" sources can be allowed to be presented to the user in all cases except for when it is determined that the user is in a public setting or at a public event. The determination of the public setting could be based on a detection of crowd noise level, a location of the user based on geolocation data, or other types of sensor data suitable for making such determinations. As another example, it may be specified that notifications from "private" sources be presented only when the user has arrived at his residence. In other cases, a gradient of priority levels can be specified for a plurality of sources, and certain events can be specified as having different levels of priority or importance. In this way, certain notifications may be allowed to be presented while the user is engaged in exercise, but may not be allowed when the user is driving, as merely one example.

Figure 7:
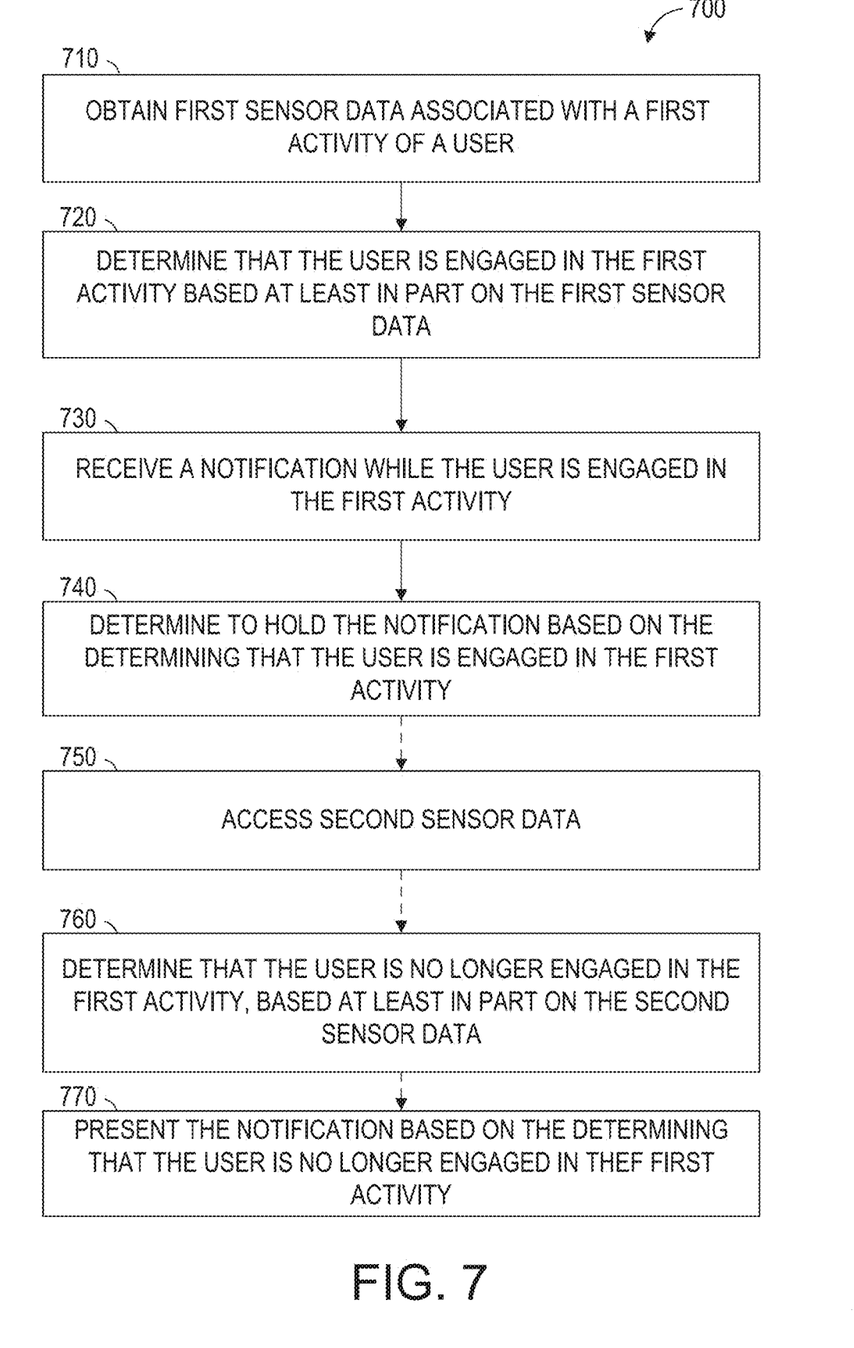
FIG. 7 is a flowchart illustrating example operations for providing notifications based on user activity data, according to some example embodiments.

Referring to FIG. 7, a flowchart illustrates an example methodology 700 for determining when to present or provide notifications to a user, based on user activity, according to aspects of the present disclosure. The example methodology 700 may be consistent with the methods described herein, including, for example, the descriptions in FIGS. 1-6.

At block 710, a device may obtain sensor data associated with a first activity of a user. The device can be a mobile device, such as the mobile device 100, or a wearable device, such as the wearable devices 200, 210, and 220, or any other device configured to obtain sensor data associated with the first activity of a user. Example types of sensor data and example means for obtaining the sensor data may include any of the descriptions of sensor data associated with any of the examples sensors described in FIG. 3, although other types of sensor data apparent to those with skill in the art can apply. Examples of the activity by the user can include any of the example activities described in FIG. 4, or any other kinds of activities apparent to those with skill in the art.

At block 720, the device may determine that the user is engaged in the first activity based at least in part on the sensor data. Example methods for determining, or at least estimating that the user is engaged in the first activity can include the example methods described in FIG. 4. Other methods for determining or at least estimating the user activity based on the obtained sensor data are possible and may be apparent to those with skill in the art, and embodiments are not so limited. Example means for making said determination may include the processor 110 via sensor data from sensor module 160 and other descriptions provided in FIG. 4.

At block 730, the device may receive a notification while the user is engaged in the first activity. The device may receive the notification through a wireless receiver included in the device, through an application on the device that provides notification based on a timer or some virtual event, or through other means for receiving notifications apparent to those with skill in the art. Example notifications can include text messages, voicemail, email, notifications in applications or websites, auction notifications, and the like. It is noted here that while the device may receive the notification, it may not necessarily display, present, or otherwise provide the notification accessible to the user while the user is engaged in the first activity.

At block 740, the device may determine to not present or in other words, hold the notification based on the determining that the user is engaged in the first activity. Example determinations to hold the notification may be consistent with any of the descriptions in FIG. 4. Example means for determining to hold the notification may include the processor 110 via sensors from sensor module 160 and any of the descriptions for making said determination in FIG. 4. In general, the determination to hold the notification while the user is engaged in the first activity is in an attempt to not distract the user during the first activity, or otherwise having it be predetermined that it will not be appropriate to provide the notification to the user during the first activity. In some example embodiments, it can be specified during which activities that the user should not receive notifications, while in other cases at least some activities can already be predetermined to not have notifications be provided during that time. In some example embodiments, override settings may be received in the device to specify which notifications may still be received when they would otherwise be normally withheld until later.

At block 750, in some example embodiments, optionally, the device may access second sensor data. The second sensor data may be associated with the user no longer being engaged in the first activity. As merely some examples, the second sensor data may be indicative of the user now being engaged in a resting state, stopping in his vehicle, or moving to a quieter place, since the first activity may involve the user in a more active and focused state. The second sensor data may be obtained by the same sensors that obtained the first sensor data, but in other cases some or all of the sensors could be different.

At block 760, optionally, the device, e.g., through the processor 110, may determine that the user is no longer engaged in the first activity, based at least in part on the second sensor data. The means for making this determination may be consistent with the example methods described in FIG. 4, and may be consistent with or analogous to the descriptions in block 720.

At block 770, optionally, having determined that the user is no longer engaged in the first activity, the device may present, display, or provide the notification, e.g., through the processor 110 and display 150, when the user is no longer engaged in the first activity. Means for presenting, displaying, or providing the notification may be consistent with any of the known methods for presenting the notification, and may also be consistent with example displays described in FIGS. 5 and 6.

Figure 8:
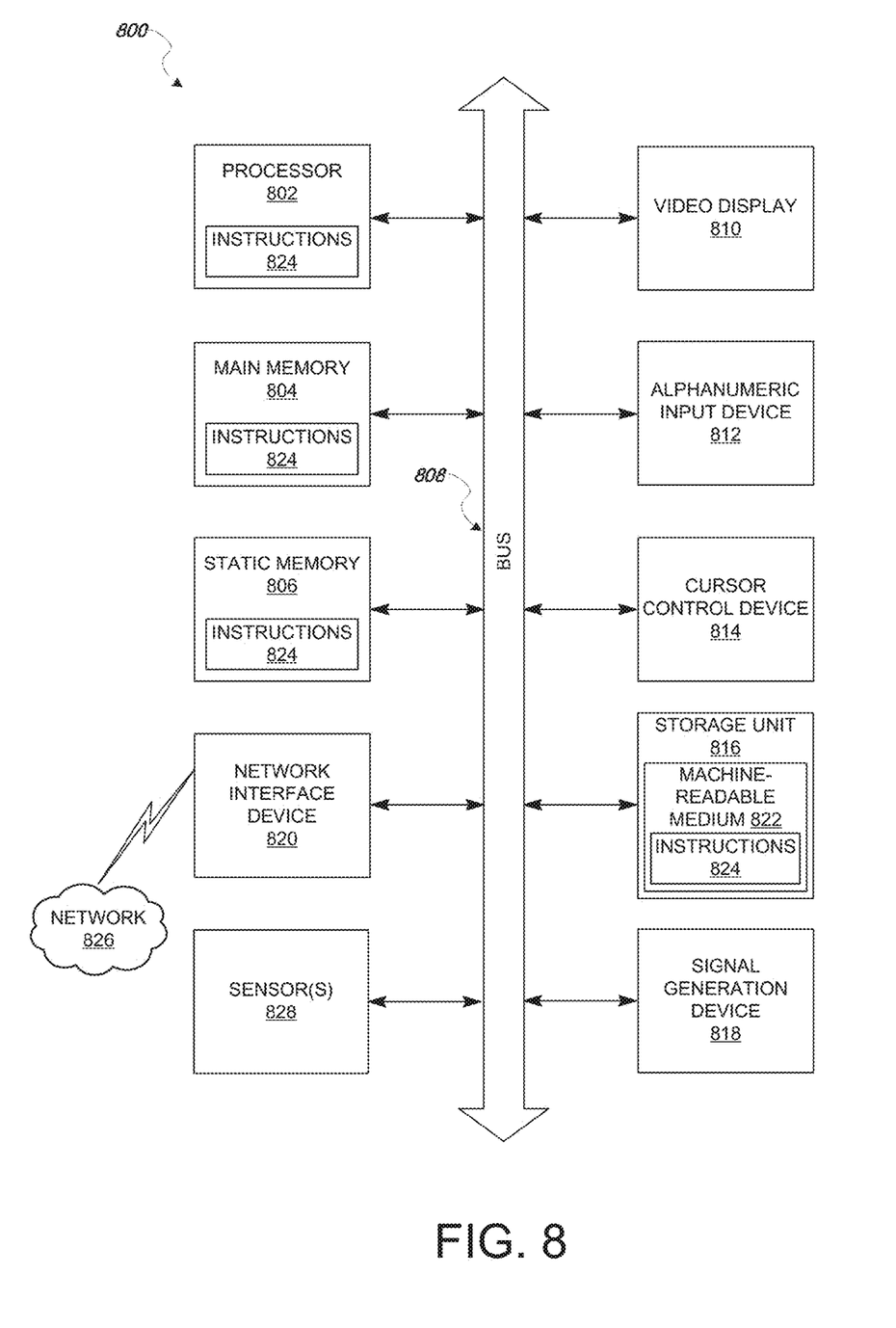
FIG. 8 is a block diagram illustrating components of a machine, according to some example embodiments, able to read instructions from a machine-readable medium and perform any one or more of the methodologies discussed herein.

Referring to FIG. 8, the block diagram illustrates components of a machine 800, according to some example embodiments, able to read instructions 824 from a machine-readable medium 822 (e.g., a non-transitory machine-readable medium, a machine-readable storage medium, a computer-readable storage medium, or any suitable combination thereof) and perform any one or more of the methodologies discussed herein, in whole or in part. Specifically, FIG. 8 shows the machine 800 in the example form of a computer system (e.g., a computer) within which the instructions 824 (e.g., software, a program, an application 140, an applet, an app, or other executable code) for causing the machine 800 to perform any one or more of the methodologies discussed herein may be executed, in whole or in part.

In alternative embodiments, the machine 800 operates as a standalone device or may be connected (e.g., networked) to other machines. In a networked deployment, the machine 800 may operate in the capacity of a server machine or a client machine in a server-client network environment, or as a peer machine in a distributed (e.g., peer-to-peer) network environment. The machine 800 may include hardware, software, or combinations thereof, and may as examples be a server computer, a client computer, a personal computer (PC), a tablet computer, a laptop computer, a netbook, a cellular telephone, a smartphone, a set-top box (STB), a personal digital assistant (PDA), a web appliance, a network router, a network switch, a network bridge, or any machine capable of executing the instructions 824, sequentially or otherwise, that specify actions to be taken by that machine. Further, while only a single machine 800 is illustrated, the term "machine" shall also be taken to include any collection of machines 800 that individually or jointly execute the instructions 824 to perform all or part of any one or more of the methodologies discussed herein.

The machine 800 includes a processor 802 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 804, and a static memory 806, which are configured to communicate with each other via a bus 808. The processor 802 may contain microcircuits that are configurable, temporarily or permanently, by some or all of the instructions 824, such that the processor 802 is configurable to perform any one or more of the methodologies described herein, in whole or in part. For example, a set of one or more microcircuits of the processor 802 may be configurable to execute one or more modules (e.g., software modules) described herein.

The machine 800 may further include one or more sensors 828, suitable for obtaining various sensor data. The machine 800 may further include a video display 810 (e.g., a plasma display panel (PDP), a light emitting diode (LED) display, a liquid crystal display (LCD), a projector, a cathode ray tube (CRT), or any other display capable of displaying graphics or video). The machine 800 may also include an alphanumeric input device 812 (e.g., a keyboard or keypad), a cursor control device 814 (e.g., a mouse, a touchpad, a trackball, a joystick, a motion sensor, an eye tracking device, or other pointing instrument), a storage unit 816, a signal generation device 818 (e.g., a sound card, an amplifier, a speaker, a headphone jack, or any suitable combination thereof), and a network interface device 820.

The storage unit 816 includes the machine-readable medium 822 (e.g., a tangible and non-transitory machine-readable storage medium) on which are stored the instructions 824 embodying any one or more of the methodologies or functions described herein, including, for example, any of the descriptions of FIGS. 1-7. The instructions 824 may also reside, completely or at least partially, within the main memory 804, within the processor 802 (e.g., within the processor's cache memory), or both, before or during execution thereof by the machine 800. The instructions may also reside in the static memory 806.

Accordingly, the main memory 804 and the processor 802 may be considered machine-readable media 822 (e.g., tangible and non-transitory machine-readable media). The instructions 824 may be transmitted or received over a network 826 via the network interface device 820. For example, the network interface device 820 may communicate the instructions 824 using any one or more transfer protocols (e.g., Hypertext Transfer Protocol (HTTP)). The machine 800 may also represent example means for performing any of the functions described herein, including the processes described in FIGS. 1-7.

In some example embodiments, the machine 800 may be a portable computing device, such as a smart phone or tablet computer, and have one or more additional input components (e.g., sensors or gauges), not shown. Examples of such input components include an image input component (e.g., one or more cameras), an audio input component (e.g., a microphone), a direction input component (e.g., a compass), a location input component (e.g., a GPS receiver), an orientation component (e.g., a gyroscope), a motion detection component (e.g., one or more accelerometers), an altitude detection component (e.g., an altimeter), and a gas detection component (e.g., a gas sensor). Inputs harvested by any one or more of these input components may be accessible and available for use by any of the modules described herein.

As used herein, the term "memory" refers to a machine-readable medium 822 able to store data temporarily or permanently and may be taken to include, but not be limited to, RAM, read-only memory (ROM), buffer memory, flash memory, and cache memory. While the machine-readable medium 822 is shown in an example embodiment to be a single medium, the term "machine-readable medium" should be taken to include a single medium or multiple media (e.g., a centralized or distributed database, or associated caches and servers) able to store instructions 824. The term "machine-readable medium" shall also be taken to include any medium, or combination of multiple media, that is capable of storing the instructions 824 for execution by the machine 800, such that the instructions 824, when executed by one or more processors of the machine 800 (e.g., processor 802), cause the machine 800 to perform any one or more of the methodologies described herein, in whole or in part. Accordingly, a "machine-readable medium" refers to a single storage apparatus or device, as well as cloud-based storage systems or storage networks that include multiple storage apparatus or devices. The term "machine-readable medium" shall accordingly be taken to include, but not be limited to, one or more tangible (e.g., non-transitory) data repositories in the form of a solid-state memory, an optical medium, a magnetic medium, or any suitable combination thereof.

Furthermore, the machine-readable medium is non-transitory in that it does not embody a propagating signal. However, labeling the tangible machine-readable medium as "non-transitory" should not be construed to mean that the medium is incapable of movement—the medium should be considered as being transportable from one physical location to another. Additionally, since the machine-readable medium is tangible, the medium may be considered to be a machine-readable device.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute software modules (e.g., code stored or otherwise embodied on a machine-readable medium 822 or in a transmission medium), hardware modules, or any suitable combination thereof. A "hardware module" is a tangible (e.g., non-transitory) unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors 802) may be configured by software (e.g., an application 140 or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a field programmable gate array (FPGA) or an ASIC. A hardware module may also include programmable logic or circuitry that is temporarily configured by software to perform certain operations. For example, a hardware module may include software encompassed within a general-purpose processor 802 or other programmable processor 802. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, and such a tangible entity may be physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor 802 configured by software to become a special-purpose processor, the general-purpose processor 802 may be configured as respectively different special-purpose processors (e.g., comprising different hardware modules) at different times. Software (e.g., a software module) may accordingly configure one or more processors 802, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors 802 that are temporarily configured (e.g., by software) or permanently configured to perform the relevant operations. Whether temporarily or permanently configured, such processors 802 may constitute processor-implemented modules that operate to perform one or more operations or functions described herein. As used herein, "processor-implemented module" refers to a hardware module implemented using one or more processors 802.

Similarly, the methods described herein may be at least partially processor-implemented, with a processor 802 being an example of hardware. For example, at least some of the operations of a method may be performed by one or more processors 802 or processor-implemented modules. As used herein, "processor-implemented module" refers to a hardware module in which the hardware includes one or more processors 802. Moreover, the one or more processors 802 may also operate to support performance of the relevant operations in a "cloud computing" environment or as a "software as a service" (SaaS). For example, at least some of the operations may be performed by a group of computers (as examples of machines 800 including processors), with these operations being accessible via a network 826 (e.g., the Internet) and via one or more appropriate interfaces (e.g., an application program interface (API)).

Some portions of the subject matter discussed herein may be presented in terms of algorithms or symbolic representations of operations on data stored as bits or binary digital signals within a machine memory (e.g., a computer memory). Such algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine 800. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine 800 (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

What is claimed is:

1. A method comprising:
   accessing, in a device, first sensor data associated with a first activity of a user;
   determining, by a hardware processor, that the user is engaged in the first activity based at least in part on the first sensor data;
   receiving, by the device, a notification while the user is engaged in the first activity;
   determining to hold the notification based on the determining that the user is engaged in the first activity;
   accessing second sensor data associated with the user;
   determining that the user is no longer engaged in the first activity based at least in part on the second sensor data;
   presenting, by the device, the notification based on the determining that the user is no longer engaged in the first activity;
   receiving, by the device, a second notification while the user is engaged in the first activity;
   accessing a second priority specification associated with the second notification, the second priority specification indicating a level of priority for presenting the second notification compared to other notifications;
   determining to present the second notification on the device while the user is engaged in the first activity based on the second priority specification; and
   receiving, at the device a setting indicting that auction notifications be identified as high priority within a predetermined amount of time of an expiration of an associated auction, wherein the second notification comprises an auction notification; and wherein the determining to present the second notification on the device is based on the predetermined amount of time until the expiration of the associated auction.

2. The method of claim 1, further comprising:
   accessing a priority specification associated with the notification, the priority specification indicating a level of priority for presenting the notification compared to other notifications.

3. The method of claim 2, further comprising:
   determining to hold the notification on the device while the user is engaged in the first activity based on the priority specification.

4. The method of claim 1, wherein the sensor data includes biometric data associated with the user's current state of health.

5. The method of claim 4, wherein the determining to hold the notification on the device while the user is engaged in the first activity is based on the biometric data satisfying a predetermined threshold level of health of the user.

6. The method of claim 1, wherein the determining to hold the notification on the device while the user is engaged in the first activity is based on determining that the user is driving a vehicle.

7. The method of claim 1 further comprising:
   determining, that the auction notification is outside the predetermined amount of time until the expiration of the associated auction;
   monitoring the predetermined amount of time until the expiration of the associated auction during the first activity; and
   determining to present the second notification on the device based on the predetermined amount of time until the expiration of the associated auction occurring while the user is engaged in the first activity.

8. A system comprising:
   a sensor configured to obtain first sensor data associated with a first activity of a user; one or more processors configured to: access the first sensor data, and
   determine that the user is engaged in the first activity based at least, in part on the first sensor data;
   a receiver configured to receive a notification while the user is engaged in the first activity;
   the one or more processors further configured to determine to hold the notification based on the user being engaged in the first activity;
   wherein the receiver is further configured to receive a second notification while the user is engaged in the first activity; and wherein the processor is further configured to:
    access a second priority specification associated with the second notification, the second priority specification indicating a level of priority for presenting the second notification compared to other notifications, and determine to present the second notification on the device while the user is engaged in the first, activity based on the second priority specification;
wherein the receiver is further configured to receive, at the device a setting indicting that auction notifications be identified as high priority within a predetermined amount of time of an expiration of an associated auction, wherein the second notification comprises an auction notification; and wherein the determining to present the second notification on the device is based on the predetermined amount of time until the expiration of the associated auction.

9. The system of claim 8, wherein the processor is further configured to:
    access second sensor data associated with the user;
    determine that the user is no longer engaged in the first activity based at least in part on the second sensor data; and
    present the notification based on the user no longer being engaged in the first activity.

10. The system of claim 8, wherein the processor is further configured to:
    access a priority specification associated with the notification, the priority specification indicating a level of priority for presenting the notification compared to other notifications.

11. The system of claim 10, wherein a determination to hold the notification while the user is engaged in the first activity is based on the priority specification.

12. The system of claim 8, wherein the sensor data includes biometric data associated with the user's current state of health.

13. The system of claim 12, wherein a determination to hold the notification while the user is engaged in the first activity is based on the biometric data satisfying a predetermined threshold level of health of the user.

14. The system of claim 8, wherein a determination to hold the notification while the user is engaged in the first activity is based on determining that the user is driving a vehicle.

15. A non-transitory computer-readable medium having no transitory signals and embodying instructions that, when executed by a processor of a machine, cause the machine to perform operations comprising:
    accessing, from one or more first sensors in a device, first sensor data associated with a first activity of a user;
    determining that the user is engaged in the first activity based at least in part on the first sensor data;
    receiving a notification while the user is engaged in the first activity;
    determining to hold the notification based on the determining that the user is engaged in the first activity;
    accessing, from one or more second sensors in the device, second sensor data associated with the user;
    determining that the user is no longer engaged in the first activity, based at least in part on the second sensor data;
    presenting the notification based on the determining that the user is no longer engaged in the first activity;
    receiving a second notification while the user is engaged in the first activity:
    accessing a second priority specification associated with the second notification, the second priority specification indicating a level of priority for presenting the second notification compared to other notifications;
    determining to present the second notification on the device while the user is engaged in the first activity based on the second priority specification; and
    receiving, at the device a setting indicting that auction notifications be identified as high priority within a predetermined amount of time of an expiration of an associated auction, wherein the second notification comprises an auction notification; and wherein the determining to present the second notification on the device is based on the predetermined amount of time until the expiration of the associated auction.

16. The non-transitory computer-readable medium of claim 15, wherein the operations further comprise:
    accessing a priority specification associated with the notification, the priority specification indicating a level of priority for presenting the notification compared to other notifications.

17. The non-transitory computer-readable medium of claim 16, wherein the determining to hold the notification on the device while the user is engaged in the first activity is based on the priority specification.

18. The non-transitory computer-readable medium of claim 15, wherein the determining to hold the notification on the device while the user is engaged in the first activity is based on determining that the user is driving a vehicle.

* * * * *